(12) United States Patent
Inman et al.

(10) Patent No.: US 9,075,011 B2
(45) Date of Patent: Jul. 7, 2015

(54) IRREGULAR EXCITATION OF OPTICAL SENSORS

(76) Inventors: Samuel Walker Inman, Boston, MA (US); Ian W. Hunter, Lincoln, MA (US)

( * ) Notice: Subject to any disclaimer, the term of this patent is extended or adjusted under 35 U.S.C. 154(b) by 0 days.

(21) Appl. No.: 14/118,303

(22) PCT Filed: May 18, 2012

(86) PCT No.: PCT/US2012/038540
§ 371 (c)(1),
(2), (4) Date: Nov. 18, 2013

(87) PCT Pub. No.: WO2012/159013
PCT Pub. Date: Nov. 22, 2012

(65) Prior Publication Data
US 2014/0084181 A1    Mar. 27, 2014

Related U.S. Application Data (60) Provisional application No. 61/487,428, filed on May 18, 2011, provisional application No. 61/648,279, filed on May 17, 2012.

(51) Int. Cl.
| | | |
|---|---|---|
| G01N 21/64 | (2006.01) | |
| G01J 3/02 | (2006.01) | |
| G01J 3/44 | (2006.01) | |
| G01N 21/77 | (2006.01) | |

(52) U.S. Cl.
CPC ............ *G01N 21/64* (2013.01); *G01J 3/0218* (2013.01); *G01J 3/4406* (2013.01); *G01N 21/6408* (2013.01); *G01N 21/7703* (2013.01); *G01N 2021/6432* (2013.01); *G01N 2021/6484* (2013.01); *G01N 2021/772* (2013.01); *G01N 2021/7786* (2013.01); *G01N 2201/0691* (2013.01)

(58) Field of Classification Search
CPC ........................................................ G01N 21/64
USPC ................................... 250/459.1, 458.1, 216
See application file for complete search history.

(56) References Cited

U.S. PATENT DOCUMENTS

| | | |
|---|---|---|
| 3,714,437 A | 1/1973 | Kinsel |
| 4,198,567 A | 4/1980 | Eneroth et al. |
| 5,329,467 A | 7/1994 | Nagamune et al. |
| 5,345,453 A | 9/1994 | Bayer et al. |
| 6,526,365 B1 | 2/2003 | Marino et al. |

(Continued)

FOREIGN PATENT DOCUMENTS

| | | |
|---|---|---|
| WO | 99/23476 | 5/1999 |

OTHER PUBLICATIONS

Chen et al., "Fluorescence Lifetime-Resolved Imaging," Photosynth Res. (2009) 102: 143-155.

(Continued)

*Primary Examiner* — David Porta
*Assistant Examiner* — Faye Boosalis
(74) *Attorney, Agent, or Firm* — Occhiuti & Rohlicek LLP (57) ABSTRACT

A material is excited with light whose intensity is modulated according to a modulation signal. The modulation signal includes multiple transitions between at least two intensity levels, with times of at least a first contiguous sequence of the transitions being selected according to an irregular pattern. A response of the material to the excitation is detected.

52 Claims, 5 Drawing Sheets

(56) References Cited

U.S. PATENT DOCUMENTS

| | | | |
|---|---|---|---|
| 6,900,030 | B2 | 5/2005 | Pitner et al. |
| 7,038,192 | B2 | 5/2006 | Lu et al. |
| 7,796,896 | B2 | 9/2010 | Sikora et al. |
| 8,476,846 | B1 | 7/2013 | Ess et al. |
| 2007/0273882 | A1 | 11/2007 | Smith |
| 2008/0125977 | A1 | 5/2008 | Anquetil et al. |
| 2008/0267246 | A1 | 10/2008 | Volodin et al. |
| 2009/0109809 | A1 | 4/2009 | Kuroda et al. |
| 2009/0208221 | A1 | 8/2009 | Sasai |
| 2009/0233330 | A1 | 9/2009 | Sachs et al. |
| 2010/0024526 | A1 | 2/2010 | Colvin, Jr. et al. |
| 2010/0235117 | A1 | 9/2010 | Melnyk et al. |
| 2011/0024620 | A1 | 2/2011 | Hidalgo et al. |

OTHER PUBLICATIONS

Colyer et al., "A Novel Fluorescence Lifetime Imaging System That Optimizes Photon Efficiency," Microscopy Research and Technique, 71: 201-213 (2008).

Feddersen et al., "Digital Parallel Acquisition in Frequency Domain Fluorimetry," Rev. Sci. Instrum. 60 (9), Sep. 1989.

Ljung, "System Identification: Theory for the User." Prentice-Hall Information and System Sciences Series. Pearson Education Canada, 1987, pp. 408-428.

Malachowski, et al., "Analytic Solutions to Modelling Exponential and Harmonic Functions Using Chebyshev Polynomials: Fitting Frequency-Domain Lifetime Images with Photobleaching," Journal of Microscopy, 228(3); 282-295, 2008.

Müller et al., "Double-Pulse Fluorescence Lifetime Imaging in Confocal Microscopy," Journal of Microscopy, 177(2): 171-179, 1995.

Piston et al., "Wide-Band Acousto-Optic Light Modulator for Frequency Domain Fluorometry and Phosphorimetry," Rev. Sci. Instrum. 60 (8), Aug. 1989.

Sauer et al., "Time-Resolved Identification of Individual Mononucleotide Molecules in Aqueous Solution with Pulsed Semiconductor Lasers," Bioimaging, 6 (1998) 14-24.

Squire et al., "Multiple Frequency Fluorescence Lifetime Imaging Microscopy," Journal of Microscopy, 197(2): 136-149, 2000.

Verkman et al., "Construction and Evaluation of a Frequency-Domain Epifluorescence Microscope for Lifetime and Anisotropy Decay Measurements in Subcellular Domains," Biophysical Chemistry, 40 (1991) 117-125.

Watkins et al., "A Parallel Multiharmonic Frequency-Domain Fluorometer for Measuring Excited-State Decay Kinetics Following One-, Two, or Three-Photon Excitation," Anal. Chem. 1998, 70, 3384-3396.

Domansky et al., "Perfused Multiwell Plate for 3D Liver Tissue Engineering," Lab Chip, 2010, 10, 51-58.

Nishimura et al., "Expansion of Intensity Correlation Spectroscopy for Lifetime Measurements—Application to Intracellular Oxygen Dynamics Measurements," Journal of Biomedical Optics, 2007, vol. 12(2).

Shin et al., "Cost-Effective Oxygen Gas Sensor Via Fluorescence Quenching," Multi-Disciplinary Senior Design Conference, 2009.

IRREGULAR EXCITATION OF OPTICAL SENSORS

CROSS-REFERENCE TO RELATED APPLICATIONS

This application is a National Stage of International Application No. PCT/US2012/038540 filed on May 18, 2012, which claims the benefit of U.S. Provisional Application 61/487,428, titled "Stochastic Excitation of Optical Sensors", filed on May 18, 2011, and U.S. Provisional Application 61/648,279, titled "Irregular Excitation of Optical Sensors", filed May 17, 2012. applications are incorporated herein by reference.

STATEMENT AS TO FEDERALLY SPONSORED RESEARCH

This invention was made with government support under Contract No. W81XWH-10-1-1013 (O.S.P. Project No. 6922729) awarded by the Department of Defense, and under Contract No. 5-50741 (O.S.P Project No. 6923482) awarded by NIH/UNC. The government has certain rights in the invention.

BACKGROUND

Sensors may be used to measure characteristics of an environment. For example, an optical sensor can include an optically sensitive material that has an optical response that is sensitive to a variety of possible characteristics of the environment. A light source, such as a laser or light emitting diode (LED), is used to provide the light that interacts with the optically sensitive material. For example, the optical spectrum of the light may be selected to excite a particular optical interaction in the material such as fluorescence, which responds to the excitation light according to fluorescence behavior (e.g., various excited state decay processes) that depends on one or more characteristics of the environment. Information about these characteristics can be obtained by detecting light that is emitted from the material.

SUMMARY

In one aspect, in general, an apparatus is configured to performing a measurement using a light source. The light source is configured to excite a material with light whose intensity is modulated according to a modulation signal, the modulation signal including multiple transitions between at least two intensity levels, with times of at least a first contiguous sequence of the transitions being selected according to an irregular pattern. The apparatus also includes a detector configured to detect a response of the material to the excitation.

In another aspect, in general, a method for performing a measurement includes exciting a material with light whose intensity is modulated according to a modulation signal. The modulation signal includes multiple transitions between at least two intensity levels, with times of at least a first contiguous sequence of the transitions being selected according to an irregular pattern. A response of the material to the excitation is then detected.

Aspects can have one or more of the following advantages.

A stochastic or pseudo-random excitation intensity pattern is able to spread the total excitation power (e.g., excitation light intensity integrated over time) across the duration of the measurement. This reduces the maximum required excitation intensity or alternatively fully utilizes the available excitation intensity. Furthermore, a stochastic or pseudo-random excitation intensity pattern enables a direct determination of the entire emission decay curve without requiring an assumption about the underlying model system. A stochastic binary pattern (i.e., a pattern with two intensity levels) is insensitive to a non-linearity. Alternatively, a pattern with at least three intensity levels enables the identification of a non-linearity. A long repetition period, or a non-repetitive excitation, enables greater resolution of response parameters in the frequency domain. Irregular modulation of a signal allows use of relatively few digital intensity levels (e.g., two or three levels), which facilitates simple and compact modulation circuitry. The modulation signal having multiple different times between transitions and a median time between transitions less than a decay time parameter enables efficient calculation of the response parameters without having to wait an extremely long time to average out the noise.

Other features and advantages of the invention are apparent from the following description, and from the claims.

DESCRIPTION

Figure 1:
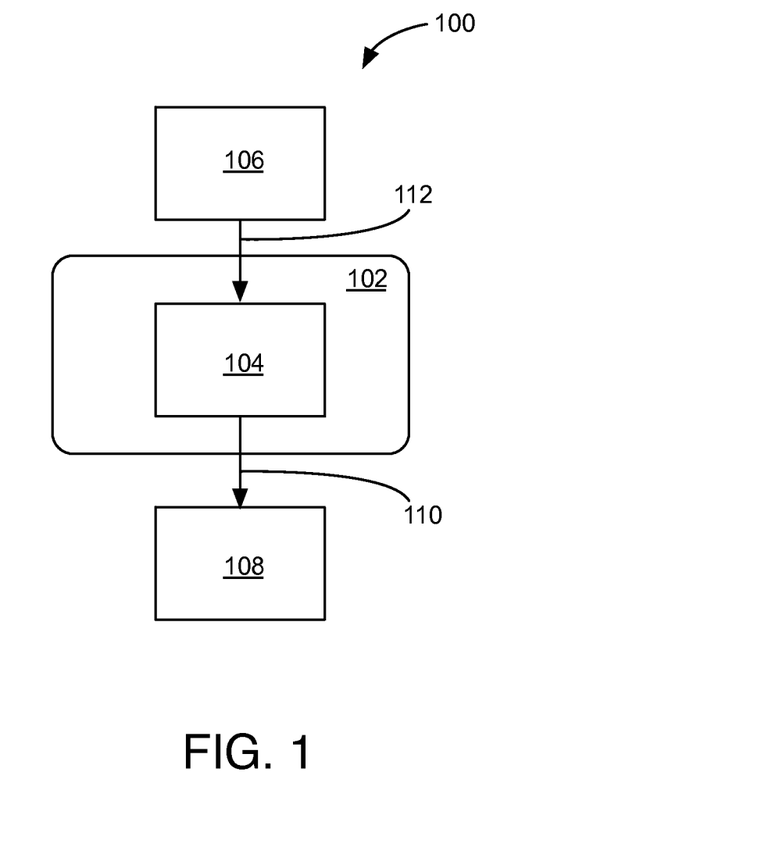
FIG. 1 is a block diagram of a sensor apparatus.

Referring to FIG. 1, a sensor apparatus 100 is configured to measure a characteristic of an environment 102. The apparatus 100 includes an optically sensitive material 104 within the environment 102, a light source 106, and a detector 108. In this example, light source 106 and detector 108 are outside of the environment 102. Alternatively, portions of the light source 106 and detector 108 can be included within the environment 102, and can be coupled to the rest of the system 100 external to the environment 102 (e.g., via wired or wireless communication). The environment 102 can be, for example, a defined volume within another device (e.g., a bioreactor). In this example, the optically sensitive material 104 is a fluorescent material that emits light 110 with a spectrum centered at a first wavelength in response to being excited by light 112 with a spectrum centered at a second wavelength shorter than the first wavelength. The emission has a temporal behavior that is characterized by a time parameter that depends on a characteristic of the environment 102. Measurement of the time parameter enables measurement of the characteristic according to this dependence. In fluorescent materials, electrons absorb photons of the excitation light 112 to transition to an excited state, and there are various pathways for the electron to relax to one or more other states. One of the relaxation pathways involves emission of a photon of the emission light 110. For a ruthenium-complex fluorescent material, another relaxation pathway involves selective quenching, due to collisions of oxygen molecules with the material, in which no emission light photon is emitted. Therefore, the temporal behavior of the detected emission light 110 is sensitive to the partial pressure of oxygen, which is the characteristic being measured in this example. In some examples, forms of optical sensitivity other than fluorescence can be used, including phosphorescence (which is another form of photoluminescence) or other non-linear optical interactions.

A variety of types of optically sensitive materials 104 can be used, which have an optical response that is sensitive to the characteristic of the environment 102 that is to be measured. These materials can be synthetic or naturally occurring, and are possibly native to the environment of interest. Optically sensitive materials can be sensitive to an environmental condition through a number of different types of interactions. For example, the quantum yield (the ratio of photons emitted to photons absorbed) of a photophysical process can depend on a concentration of a substrate of interest, or can depend on temperature. The substrate can be a quencher, for example. In some cases, the quantum yield of a photophysical process can be dependent on various forms of excited state decay. The quantum yield can be equivalently expressed as the ratio of the rate of radiative decay to the combined rate of all forms of excited state decay (both radiative and non-radiative, including quenching, Forster Resonance Energy Transfer, etc.). The term optically sensitive material parameter (OSM parameter) will refer to a measured value or a set of measured values describing the optically sensitive material 104. The OSM parameter can be correlated to a characteristic of the environment 102 that is of interest.

In order to better characterize the behavior of the optical response (e.g., especially in the presence of noise), the intensity of the excitation light 112 is controlled by the light source 106. In some implementations, the light source 106 includes a modulator (e.g., an electronic modulator) that modulates the intensity of the excitation light 112 to generate a pattern of time variation with an associated modulation spectrum. (The term wavelength will be used when describing the optical spectrum of electromagnetic radiation. It is understood that there is also a frequency associated with electromagnetic radiation of given wavelength, however, the term frequency will generally be used to characterize the relatively low-frequency modulation spectrum of the intensity modulation.) In some implementations, the time pattern of the excitation light 112 is an irregular pattern of light intensity that is selected to have particular time and frequency characteristics, as described in more detail below. In some cases, the irregular light intensity pattern is generated from a stochastic process or pseudo random code with time varying or time invariant statistical properties (e.g., using a random number generator on a computer). In some cases, the irregular light intensity pattern is selected so that it is non-periodic over a measurement time span, or such that any period over which the pattern repeats is relatively large (e.g., compared to a time related OSM parameter).

The detector 108 includes circuitry (e.g., a photodiode circuit) that generates an electronic signal proportional to the intensity of the emission light 110 captured by the detector 108. This signal may then be recorded and stored and/or passed to another device for additional processing. For example, the intensity pattern of the emission light 110 represented by the signal can be compared with an expected response, based on the known modulation applied by the modulator, in order to determine the OSM parameter associated with the characteristic of the environment 102 being measured.

Figure 2:
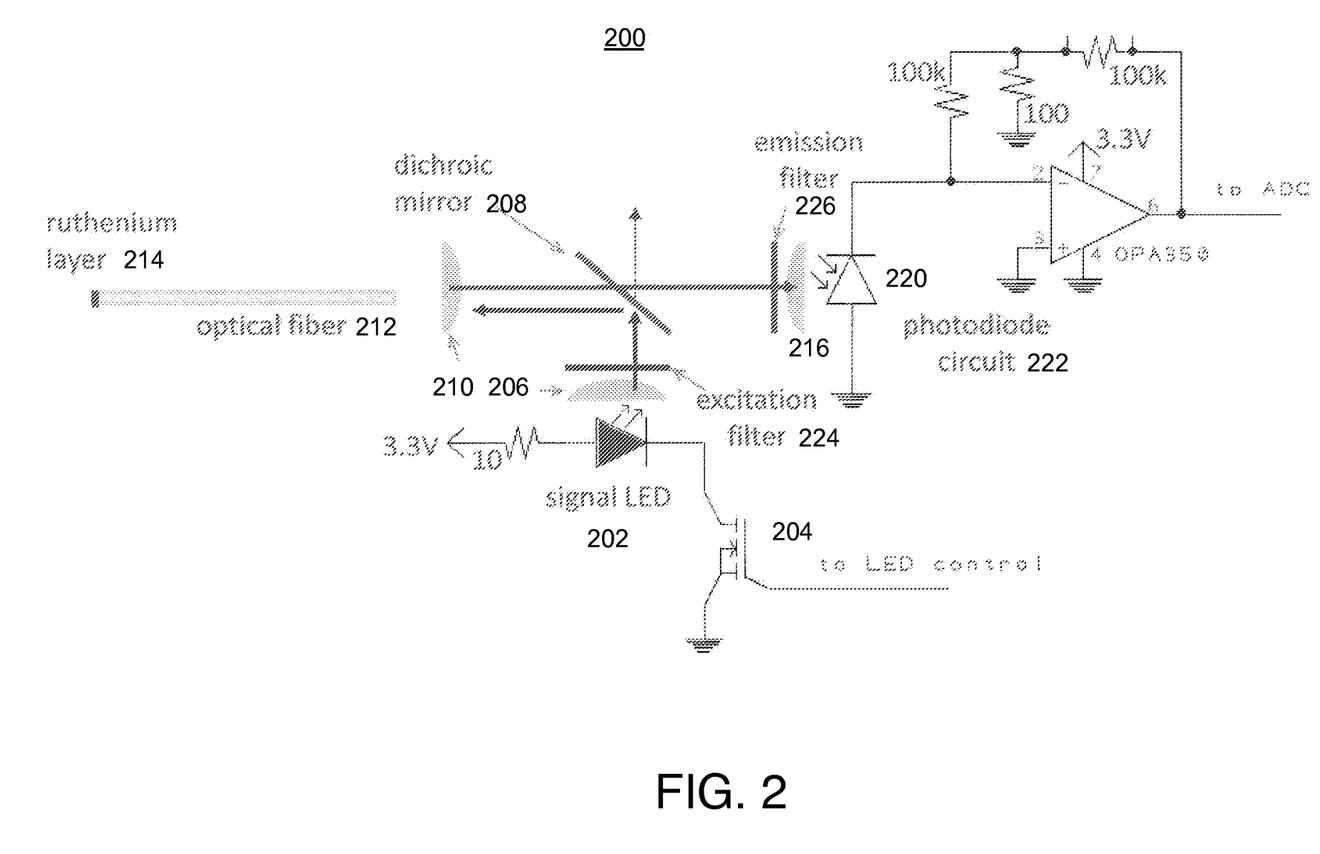
FIG. 2 is a schematic diagram of a sensor apparatus.

FIG. 2 shows a device 200, which is an example of a portion of the sensor apparatus 100. The device 200 includes a signal LED 202 that is modulated by a switch 204 (e.g., a transistor) that is controlled by an LED control signal provided by a control module (e.g., a computer, microcontroller, FPGA, clocked digital logic, etc.). Light from the signal LED 202 with the desired intensity modulation is focused by an input lens 206 and directed by a dichroic mirror 208 to a coupling lens 210, which couples the light into an optical fiber 212. One end of the optical fiber 212 includes a ruthenium layer 214 as the sensing material. This end of the optical fiber 212 is able to be positioned within the environment 102, while the rest of the device 200 is able to be positioned outside of the environment 102.

The excitation light excites the ruthenium layer 214 and emission light propagates within the fiber in the direction towards the coupling lens 210 and the dichroic mirror 208. The transmittance of the dichroic mirror 208 is selected to enable the excitation light to be substantially reflected and the emission light to be substantially transmitted. For example, the dichroic mirror 208 can be selected to transmit wavelengths between about 600 to 800 nm and reflect wavelengths between about 520 to 550 nm. The emission light is focused by an output lens 216 onto a detector that provides an electrical response signal. In this example, the detector includes a photodiode 220 and a photodiode circuit 222, which is a transimpedance amplifier converting an output current from the photodiode 220 into an amplified voltage signal sent to an analog-to-digital converter (ADC) of an analysis module (not shown). The amplified voltage signal is sampled by the ADC and converted to a series of digital values. The detected electrical response signal can be filtered to remove signal frequencies greater than half the sampling frequency before the electrical response signal is sampled. The analysis module and the control module can be implemented in the same device or in different devices, and can include one or more processors for executing instructions for performing calculations associated with the modulation signal or measurement analysis, and circuitry for interfacing with the rest of the light source and detector.

Optionally, optical filters can be used to further control the spectrum of the excitation light, and ensure that the detected emission light does not include a significant amount of the noise (e.g., leaked excitation light). Emission and excitation filters can be selected such that the ranges of wavelengths allowed to pass through the respective filters do not overlap. In this example, an excitation filter 224 is used to block a range of wavelengths coming from the signal LED 202 such that only certain wavelengths of excitation light (e.g., wavelengths less than about 535 nm) reach the ruthenium layer 214. An emission filter 226 is used to block a range of wavelengths such that only certain wavelengths of emission light (e.g., wavelengths larger than about 590 nm) reach the detector.

In other examples, various alternative implementations of various portions of the sensor apparatus can be used. For example, light sources other than an LED can be used (e.g., such as a laser). It is possible to use a constant light source in combination with a shutter or optical modulator to create the light intensity pattern. Light detectors other than a photodiode can be used (e.g., a photo-multiplier tube, a phototransistor, etc.). Multiple light sources can be used to increase the number of available excitation intensity levels. Multiple or parallel light detectors can be used to increase spatial or temporal resolution. The excitation light from the light source can be directly incident onto the sensing material, or can be focused through a lens onto the sensing material, or the sensing material can be attached to an optical fiber, as in the example above, with excitation light focused from the light source into the optical fiber. Excitation light from the light source can be reflected by a mirror or multiple mirrors including mirrors with a wavelength filtering transmittance spectrum such as dichroic mirrors. Lenses can be integrated with light sources (e.g., an LED may have a dome which serve as a lens) and also with light detectors (e.g., a photodiode may have an integrated lens). Optical filters can be coated onto glass and used as standalone components or can be coated directly onto light sources and light detectors.

The control module that determines the intensity modulation of the excitation light is able to provide an irregular intensity pattern that is generated based on a stochastic signal in the sense that the pattern has properties that appear random or pseudo random, or that are derived from random or pseudo random processes. The stochastic signal can have time varying or time invariant statistical properties. Although the stochastic signal may be generated from an underlying random signal, it is possible to generate a coded signal with similar statistical properties to a random signal that follow some rule and are pseudo random. In some implementations, the intensity pattern is generated by applying a pseudo random digital signal to a modulation control input of the light source 106 (e.g., a digital-to-analog converter (DAC) that provides a modulation signal to the switch 204). The signal provides two or more substantially discrete levels of intensity in the excitation light, based on an electronic version of the signal (e.g., a voltage or current) applied to the control input. A probability density function associated with the pseudo random code may lead to approximately equal probabilities for each of the levels or may lead to a larger probability for certain levels relative to others. The probability density function can contain a number of discrete states or it can be continuous over a certain range. Additionally, particularly for discrete signals with two or more possible excitation intensity levels, there are multiple different time intervals between transitions from one intensity level to the next. For example, transitions between the two levels of a binary signal occur at irregular intervals, with different time intervals occurring between different respective pairs of adjacent transitions (e.g., at least 10 different time intervals, or at least 5 different time intervals, or at least 3 different time intervals). The spectrum of such a modulation signal contains a range of frequencies within a modulation bandwidth. The modulation signal can be selected to have particular time characteristics in comparison to a time parameter associated with the optical interaction of the sensing material. For example, the modulation signal can be selected so that the smallest period over which the signal repeats is larger than a time over which emission from the sensing material is expected to decay (expressed as some multiple of an exponential time constant, e.g., at least 10 or 15 or 20 or 50 or 100 times the time constant). If the modulation signal does not repeat over any period, then the period of such a signal is considered to be infinite. The modulation signal can also be selected so that the root mean square intensity of the signal is at least a tenth of the maximum signal intensity. Alternatively, the excitation intensity pattern can be set such that a relatively short percentage (e.g., less than 10% to 25%) of the measurement time is spent at the lowest excitation intensity level.

Figure 3A:
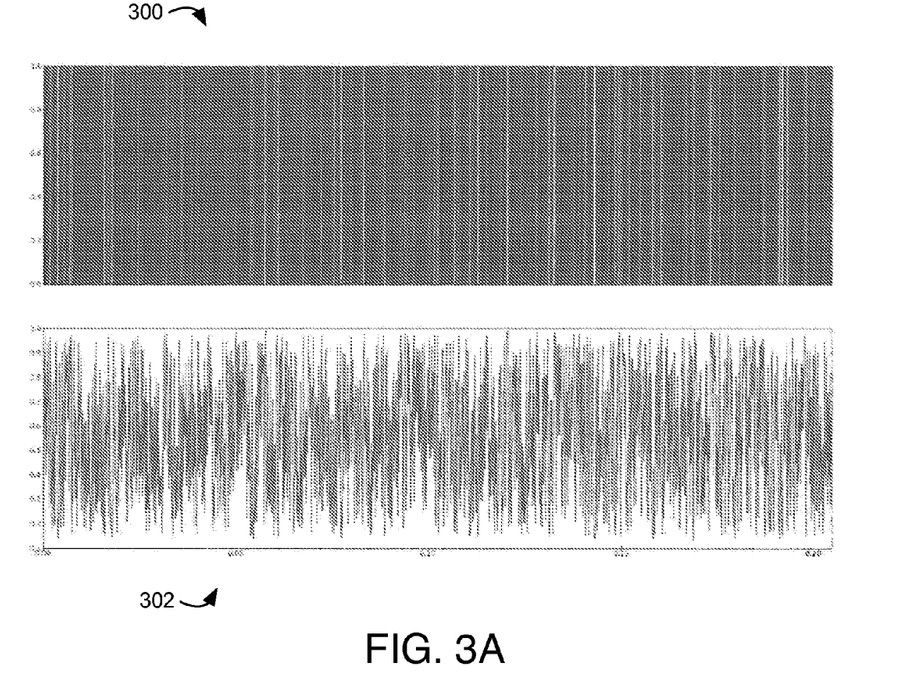
FIGS. 3A-3B are plots of excitation and emission signals.
Figure 3B:
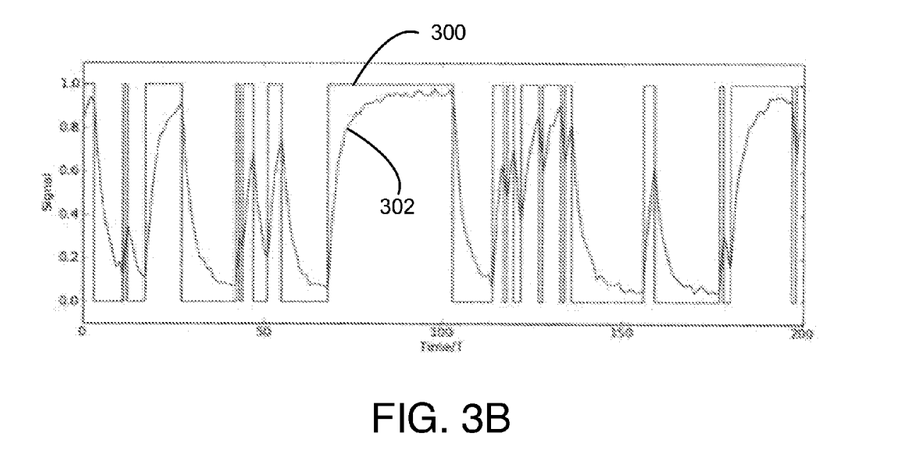

Referring to FIGS. 3A and 3B, a modulation signal 300 is a pseudo random binary signal that transitions between a zero amplitude level and a nonzero amplitude level (labeled as a normalized value of 1.0) according to a binary pseudo random code that yields approximately equal probabilities for the zero and nonzero levels. The resulting normalized response signal 302 associated with the detected emission light has time and intensity characteristics that can be analyzed to yield information about the characteristics of the environment that affect the optical response of the optically sensitive material. FIG. 3B shows the modulation signal 300 and normalized response signal 302 superimposed and zoomed in to highlight the features of the signals in FIG. 3A in more detail. As evident from both FIGS. 3A and 3B, the modulation signal 300 provides time spans of different lengths over which the excitation light is present (the 1.0 level) or not present (the 0.0 level). The resulting response signal 302 builds up according to an exponential response during the time spans in which the excitation light is present, and decays according to an exponential response during the time spans in which the excitation light is not present.

In some implementations, the irregular modulation signal is allowed to switch between these intensity levels at irregular multiples of a regular interval of time (dt) (i.e., the pattern can either switch levels or remain at the same level each interval, but the signal remains constant between intervals). In this example, the length of a period of the pattern is 20,480 samples and the time interval dt between samples is 10 microseconds. Using appropriately fast electronics the time interval between samples can be significantly reduced in order to accommodate for faster excited sate decay times.

The irregular pattern is generated, for example, by sampling a stochastic or pseudo random process with a Gaussian probability density function or another continuous or discrete probability density function with zero mean or otherwise. In some implementations, the series of values generated from such a code is filtered using a low pass filter (LPF), for example, with a time constant of five times the sample interval (dt). The signal can then be converted to a binary signal (limiting to two possible levels) by assigning all positive values to the nonzero level (1.0) and all negative values to the zero level (0.0). A signal containing any number of discrete levels can be generated by selecting an appropriate step size for transforming a continuous signal into a discrete signal. If the length of the pattern is an even number and the median values are not repeated, centering the median on zero before converting the continuous signal to a binary signal will result in a binary signal with a probability values for 0.0 and 1.0 equal to 0.5. This property can simplify algorithms for calculating OSM parameters.

Figure 4A:
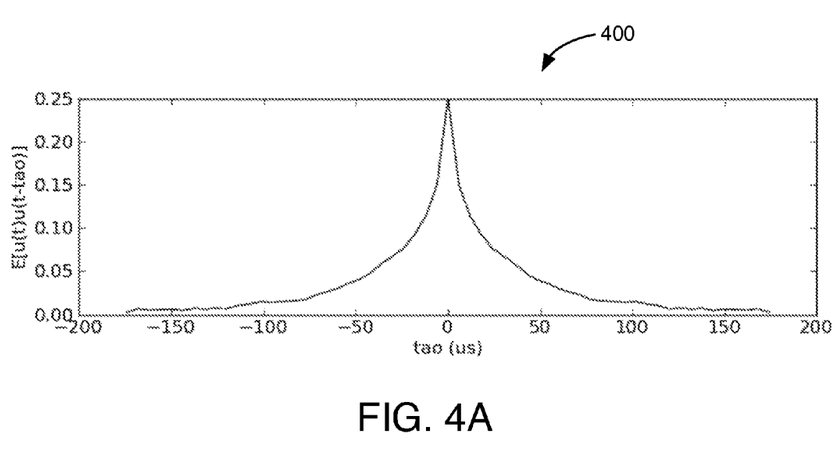
FIGS. 4A-4B are plots of the autocorrelation and the power spectrum, respectively, of an excitation intensity pattern.
Figure 4B:
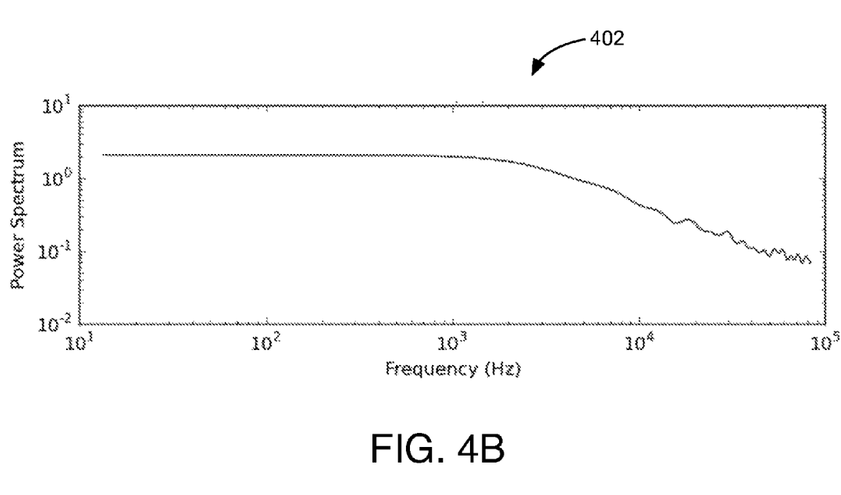

The initial series of values corresponding to a Gaussian random number has a flat power spectrum and the autocorrelation of the signal is the impulse function. The resulting stochastic nature of the modulation signal improves immunity to static nonlinearities in the system based on Bussgang's theorem. When the random Gaussian (stochastic) signal it is convolved with a LPF the power spectrum of the resulting signal is altered to decrease the energy in the modulation signal at the higher frequencies that are closer to the sampling frequency. When the filtered signal is then converted from the initial continuous Gaussian probability density function to have a probability density function containing a discrete number of values (no longer continuous), then the power spectrum of the binary signal (or digital signal when there are more than two levels) will be further altered by this conversion. An example of an autocorrelation 400 and a power spectrum 402 of an excitation intensity signal are shown in FIGS. 4A and 4B, respectively. The excitation characteristics corresponding to these plots are only optimal for a sensing material with certain time parameters and noise characteristics.

By convolving an initially pseudo random signal with a flat power spectrum with a filter, the power spectrum of the resulting input signal can be tuned such that it excites the optically sensitive material in a way that allows observation of OSM parameters that are most sensitive to the surrounding environmental conditions. Additionally, the choice of filters can be varied based on current environmental conditions such that the input pattern for each measurement is maximally informative about the current environment. Alternatively the sample interval dt can be adjusted based on current environmental conditions. Using one or more of these two approaches, the sensor can be adaptive to the environment in real time.

The sampling of the emission light from the optically sensitive material at the detector 108 can be at regular sample intervals (e.g., some number of nanoseconds to microseconds), and the sample interval can be the same interval dt at which the modulation signal increments. Alternatively the interval dt for incrementing the modulation signal can be multiple of the sampling interval at the detector. A large number of samples can be measured and recorded (e.g., 20,480 samples), or the samples can be processed as they occur.

Multiple measurements can be obtained, and thus the sensor can be used to monitor an environmental condition. In this configuration there is a distinct period (i.e., time interval) between one measurement and a subsequent measurement. With respect to measurements associated with the time varying properties of an excitation signal, the excitation signal can be maintained in any arbitrary state during the interval between measurements.

The analysis module analyzes the detected response signal based on the known modulation signal to determine characteristics of the environment 102. The OSM parameter or parameters can be estimated and calibrated to the environmental condition. Although one possible use of the OSM parameters is to describe a state of the environment, it is often useful to calculate the OSM parameters based on the accuracy with which they can predict the measured response of the optical sensing material y based on an input irregular light intensity pattern u. There are a number of techniques available for this purpose. A model can be chosen where the purpose of the model is to predict the measured response based on the known input sequence. For example, a finite impulse response FIR model predicts the measured response based on a history of previous input values and is a non-parametric model, or the autoregressive with exogenous input ARX model predicts a response based on the previous response values in addition to a series of previous inputs. A set of OSM parameters can constitute a transfer function TF, for example a set including a gain and two time constants ($G, \tau_1, \tau_2$) is a second order transfer function, that describes the optically sensitive material 104. There are advantages and disadvantages to any model structure, but ultimately the choice of OSM parameters to estimate should be guided by how well the chosen parameters correspond to an environmental condition of interest.

Using an appropriate model structure, the model parameter values can be chosen to minimize error between the measured response and a predicted response based on the model. A least squares algorithm can be used for this purpose although they are many other techniques. For real-time calculation of OSM parameters a recursive least square algorithm can be used.

Figures 5A, 5B:
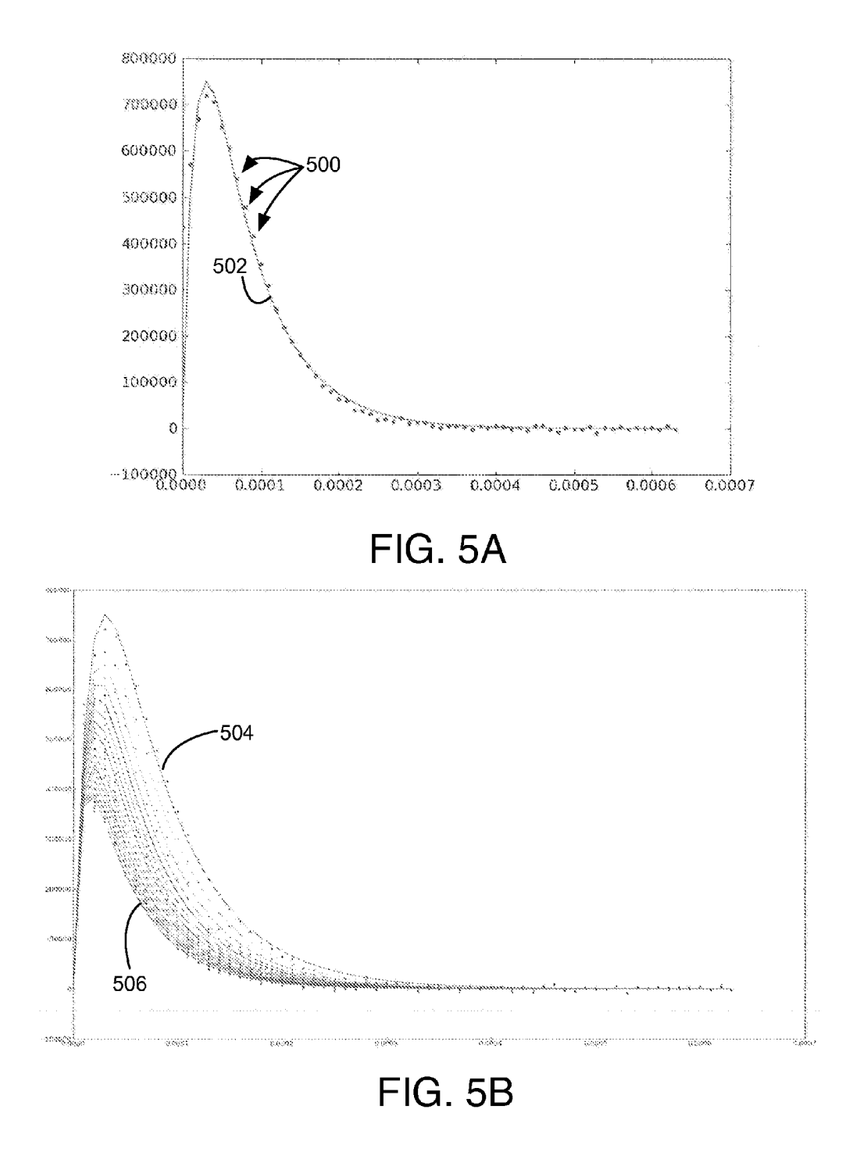
FIGS. 5A-5B are plots of impulse responses.

A comparison of the measured response y to the predicted response based on the known irregular modulation signal and a set of OSM parameters can be used to determine the quality of the OSM parameters. This comparison can also be useful for identifying a non-linearity. FIG. 5A shows measured data points (dots 500) and a corresponding best-fit second order impulse response $y=G(\exp(-t/\tau_1)-\exp(-t/\tau_2))$ (solid line 502). In general a decay curve of any order N can be described $y=\Sigma_{n=1}^{N} G_n e^{-t/\tau_n}$.

One or more OSM parameters can be measured across a range of environmental conditions of interest. An OSM parameter or combinations of selected OSM parameters can be calibrated against the environmental conditions of interest. FIG. 5B shows how the measured data points and impulse response are expected to change based on the changes in the oxygen partial pressure in the example of a ruthenium-complex optically sensitive material, over a range of pressure from 3 to 21 kPa. For a low-oxygen environment the impulse response 504 has a higher peak and longer tail than for a high-oxygen environment 506.

OSM parameters can be further converted by linear or non-linear equations and can be combined with calibration values in order to provide an estimate of an environmental condition of interest. For example, the Stern-Volmer equation $$P_{O2}=1/K_{SV}(\tau_0/\tau-1)$$

which describes how quantum yields of a photophysical process are influenced by partial pressure of a substrate or quencher (e.g., oxygen), may be used. Using this equation it is possible with appropriate calibrations to convert measured OSM parameters, in this case an exponential time constant $\tau$, to an estimation of the partial pressure of oxygen.

The techniques described above can be implemented using a program comprising instructions for execution on a device or module (e.g., the control module and/or analysis module) including one or more processors or other circuitry for executing the instructions. For example, the instructions execute procedures of software or firmware that runs on one or more programmed or programmable computing devices or modules including at least one processor and at least one data storage system (e.g., including volatile and non-volatile memory, and/or storage media). The programs may be provided on a computer-readable storage medium, such as a CD-ROM, readable by a general or special purpose programmable computer or delivered over a communication medium such as network to a computer where it is executed. Each such program may be stored on or downloaded to a storage medium (e.g., solid state memory or media, or magnetic or optical media) readable by a computing device, for configuring and operating the device when the storage medium is read by the device to perform the procedures of the program.

It is to be understood that the foregoing description is intended to illustrate and not to limit the scope of the invention, which includes the scope of the appended claims. Other embodiments are within the scope of the following claims.

What is claimed is:

1. An apparatus for performing a measurement, the apparatus comprising:
    a light source configured to excite a material with light whose intensity is modulated according to a modulation signal, the modulation signal including multiple transitions between at least two intensity levels, with times of at least a first contiguous sequence of the transitions being selected according to an irregular pattern; and
    a detector configured to detect a response of the material to the excitation;
    wherein performing the measurement includes calculating an optically sensitive material parameter based on the detection of the response of the material to the excitation.

2. The apparatus of claim 1, further comprising the material, where the material has an optical response that is sensitive to a characteristic of an environment and is characterized by at least one time parameter.

3. The apparatus of claim 2, the wherein the irregular pattern comprises a pattern having an median time between adjacent transitions, over the time span covered by the first contiguous sequence of the transitions, less than the time parameter, and having a repetition period greater than twice the time parameter.

4. The apparatus of claim 2, wherein the time parameter is based on an exponential time constant that characterizes decay of fluorescence emission from the material after being excited by light.

5. The apparatus of claim 4, wherein the modulation signal has a peak intensity level that is less than about ten times a root mean square intensity level over the time span covered by the first contiguous sequence of the transitions, and the irregular pattern has a repetition period greater than about ten times the exponential time constant.

6. The apparatus of claim 4, wherein the time parameter is based on the longest of multiple exponential time constants that characterize decay of fluorescence emission from the material after being excited by light.

7. The apparatus of claim 4, wherein the time parameter is greater than about ten times the exponential time constant.

8. The apparatus of claim 7, wherein the median time between adjacent transitions is less than about half of the time parameter.

9. The apparatus of claim 8, wherein the irregular pattern has a repetition period greater than about two times the time parameter.

10. The apparatus of claim 2, wherein the characteristic of the environment comprises a quantity of a molecule.

11. The apparatus of claim 10, wherein the quantity of the molecule comprises a partial pressure of a gas of the molecule.

12. The apparatus of claim 1, wherein the irregular pattern comprises at least four different time intervals between different respective pairs of adjacent transitions in the sequence.

13. The apparatus of claim 1, wherein the irregular pattern comprises a pattern determined according to a stochastic process or a psesudo random code.

14. The apparatus of claim 13, wherein determining the pattern according to the stochastic process or pseudo random code comprises filtering a series of random or pseudo random values and generating intensity values of the modulation signal based on the filtered random or pseudo random values at multiples of a time interval.

15. The apparatus of claim 14, wherein the filtering comprises low-pass filtering.

16. The apparatus of claim 15, wherein a time constant inversely proportional to a cutoff frequency of the low-pass filtering is at least twice the time interval.

17. The apparatus of claim 1, wherein the modulation signal is a binary signal having transitions between two intensity levels.

18. The apparatus of claim 17, wherein the time over which each transition occurs is shorter than the time between adjacent transitions.

19. The apparatus of claim 17, wherein the irregular pattern comprises at least four different time intervals between different respective pairs of adjacent transitions in the sequence.

20. The apparatus of claim 17, wherein the fraction time at the lower of the two intensity levels, over the time span covered by the first sequence of the transitions, is less than 0.9.

21. The apparatus of claim 17, wherein the fraction time at the higher of the two intensity levels, over the time span covered by the first sequence of the transitions, is greater than 0.1.

22. The apparatus of claim 17, wherein one of the two intensity levels is a zero intensity level.

23. The apparatus of claim 1, wherein the modulation signal is a ternary signal having transitions between three intensity levels.

24. The apparatus of claim 23, wherein the time over which each transition occurs is shorter than the time between adjacent transitions.

25. The apparatus of claim 23, wherein the irregular pattern comprises at least four different time intervals between different respective pairs of adjacent transitions in the sequence.

26. The apparatus of claim 23, wherein the fraction time at the lowest of the three intensity levels, over the time span covered by the first sequence of the transitions, is less than 0.9.

27. The apparatus of claim 23, wherein the fraction time at the highest of the three intensity levels, over the time span covered by the first sequence of the transitions, is greater than 0.1.

28. The apparatus of claim 23, wherein one of the three intensity levels is a zero intensity level.

29. The apparatus of claim 1, wherein the modulation signal includes multiple transitions between at most sixteen intensity levels.

30. The apparatus of claim 1, wherein detecting the response of the material to the excitation includes detecting emitted light from a non-linear optical interaction of the excitation light with the material.

31. The apparatus of claim 1, wherein the calculating includes measuring changes in a response signal that builds up according to an exponential response during time spans in which the excitation light is present at the material, and decays according to an exponential response during time spans in which the excitation light is not present at the material.

32. The apparatus of claim 1, wherein the calculating includes comparing a detected response to a predicted response based on the irregular pattern to identify a non-linearity.

33. A method for performing a measurement, the method comprising:
exciting a material with light whose intensity is modulated according to a modulation signal, the modulation signal including multiple transitions between at least two intensity levels, with times of at least a first contiguous sequence of the transitions being selected according to an irregular pattern; and
detecting a response of the material to the excitation;
wherein performing the measurement includes calculating an optically sensitive material parameter based on the detection of the response of the material to the excitation.

34. The method of claim 33, further comprising providing the material, where the material has an optical response that is sensitive to a characteristic of an environment and is characterized by at least one time parameter.

35. The method of claim 34, the wherein the irregular pattern comprises a pattern having an median time between adjacent transitions, over the time span covered by the first contiguous sequence of the transitions, less than the time parameter, and having a repetition period greater than twice the time parameter.

36. The method of claim 34, wherein the time parameter is based on an exponential time constant that characterizes decay of fluorescence emission from the material after being excited by light.

37. The method of claim 36, wherein the modulation signal has a peak intensity level that is less than about ten times a root mean square intensity level over the time span covered by the first contiguous sequence of the transitions, and the irregular pattern has a repetition period greater than about ten times the exponential time constant.

38. The method of claim 36, wherein the time parameter is based on the longest of multiple exponential time constants that characterize decay of fluorescence emission from the material after being excited by light.

39. The method of claim 36, wherein the time parameter is greater than about ten times the exponential time constant.

40. The method of claim 39, wherein the median time between adjacent transitions is less than about half of the time parameter.

41. The method of claim 40, wherein the irregular pattern has a repetition period greater than about two times the time parameter.

42. The method of claim 34, wherein the characteristic of the environment comprises a quantity of a molecule.

43. The method of claim 42, wherein the quantity of the molecule comprises a partial pressure of a gas of the molecule.

44. The method of claim 33, wherein the irregular pattern comprises at least four different time intervals between different respective pairs of adjacent transitions in the sequence.

45. The method of claim 33, wherein the irregular pattern comprises a pattern determined according to a stochastic process or a psuedo random code.

46. The method of claim 33, wherein the modulation signal is a binary signal having transitions between two intensity levels.

47. The method of claim 46, wherein the time over which each transition occurs is shorter than the time between adjacent transitions.

48. The method of claim 46, wherein the irregular pattern comprises at least four different time intervals between different respective pairs of adjacent transitions in the sequence.

49. The method of claim 46, wherein the fraction time at the lower of the two intensity levels, over the time span covered by the first sequence of the transitions, is less than 0.9.

50. The method of claim 46, wherein the fraction time at the higher of the two intensity levels, over the time span covered by the first sequence of the transitions, is greater than 0.1.

51. The method of claim 46, wherein one of the two intensity levels is a zero intensity level.

52. An apparatus for performing a measurement, the apparatus comprising:
- a light source configured to excite a material with light whose intensity is modulated according to a modulation signal, the modulation signal including multiple transitions between at least two intensity levels, with times of at least a first contiguous sequence of the transitions being selected according to an irregular pattern; and
- a detector configured to detect a response of the material to the excitation;
- wherein detecting the response of the material to the excitation includes detecting emitted light from a non-linear optical interaction of the excitation light with the material.

* * * * *